(12) United States Patent
Shabudin et al.

(10) Patent No.: US 11,426,519 B2
(45) Date of Patent: Aug. 30, 2022

(54) INJECTION DEVICE WITH GAP REDUCTION MECHANISM

(71) Applicant: Owen Mumford Ltd., Oxfordshire (GB)

(72) Inventors: Tahir Shabudin, Oxfordshire (GB); Matthew John Dobson, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 224 days.

(21) Appl. No.: 16/494,499

(22) PCT Filed: Mar. 15, 2018

(86) PCT No.: PCT/GB2018/050663
§ 371 (c)(1),
(2) Date: Sep. 16, 2019

(87) PCT Pub. No.: WO2018/167493
PCT Pub. Date: Sep. 20, 2018

(65) Prior Publication Data
US 2020/0206423 A1 Jul. 2, 2020

(30) Foreign Application Priority Data
Mar. 15, 2017 (GB) .................................... 1704136

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/3204* (2013.01);
(Continued)

(58) Field of Classification Search
CPC ............ A61M 5/2033; A61M 5/31501; A61M 5/3204; A61M 5/3243; A61M 2005/206;
(Continued)

(56) References Cited

U.S. PATENT DOCUMENTS

| 2008/0195056 A1 | 8/2008 | Bishop et al. |
| 2015/0100031 A1 | 4/2015 | Cowe |
| 2018/0250471 A1* | 9/2018 | Grimoldby ....... A61M 5/31553 |

FOREIGN PATENT DOCUMENTS

| CN | 102123753 A | 7/2011 |
| CN | 102770173 A | 11/2012 |

(Continued)

OTHER PUBLICATIONS

First Office Action from corresponding Chinese Patent Application No. 201880032544.2 dated Apr. 30, 2021 (14 pages) (English translation included).
International Search Report, PCT/GB2018/050663, dated Aug. 6, 2018.
Great Britain Search Report, GB1704136.9, dated Aug. 11, 2017.
Written Opinion, PCT/GB2018/050663, dated Aug. 6, 2018.
(Continued)

*Primary Examiner* — Bhisma Mehta
*Assistant Examiner* — Rachel T. Smith
(74) *Attorney, Agent, or Firm* — Quarles & Brady LLP

(57) ABSTRACT

An autoinjector includes: an insertion spring between a housing and plunger assembly; a syringe driver; a second release mechanism releasing the plunger assembly from the housing, causing the insertion spring to move the plunger assembly through the housing with a syringe driver; a stop limiting movement of the syringe driver in the housing; and a third release mechanism releasing the plunger assembly from the syringe driver upon engagement with the stop, allowing the plunger assembly to continue through the housing. The first release mechanism releases the plunger from the delivery spring housing upon contact between the plunger assembly and a bung, causing the delivery spring to separate the delivery spring housing and the plunger, apply-
(Continued)

ing a delivery force to a bung. A latch mechanism latches the delivery spring housing at a forward position, preventing rearward movement of the delivery spring housing following release of the plunger.

19 Claims, 17 Drawing Sheets

(52) U.S. Cl.
CPC ..... *A61M 5/3243* (2013.01); *A61M 2005/206* (2013.01); *A61M 2005/208* (2013.01); *A61M 2005/2086* (2013.01); *A61M 2005/3247* (2013.01)

(58) Field of Classification Search
CPC .... A61M 2005/208; A61M 2005/2086; A61M 2005/3247
See application file for complete search history.

(56) References Cited

FOREIGN PATENT DOCUMENTS

| | | |
|---|---|---|
| EP | 2 489 380 | 8/2012 |
| GB | 2 538 566 | 11/2016 |
| WO | WO 2009/022132 | 2/2009 |
| WO | WO 2011/101381 | 8/2011 |
| WO | WO 2012/049484 | 4/2012 |
| WO | WO 2012/085580 | 6/2012 |
| WO | WO 2015/011488 | 1/2015 |
| WO | WO 2016/189286 | 12/2016 |
| WO | WO-2016189286 A1 * | 12/2016 .............. A61M 5/20 |
| WO | WO 2017/187140 | 11/2017 |

OTHER PUBLICATIONS

International Preliminary Report on Patentability for International Patent Application, PCT/GB2018/050663, dated Sep. 26, 2019.

* cited by examiner

PRIOR ART  Figure 1

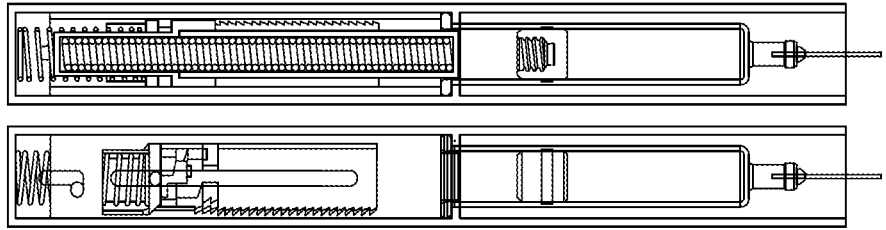
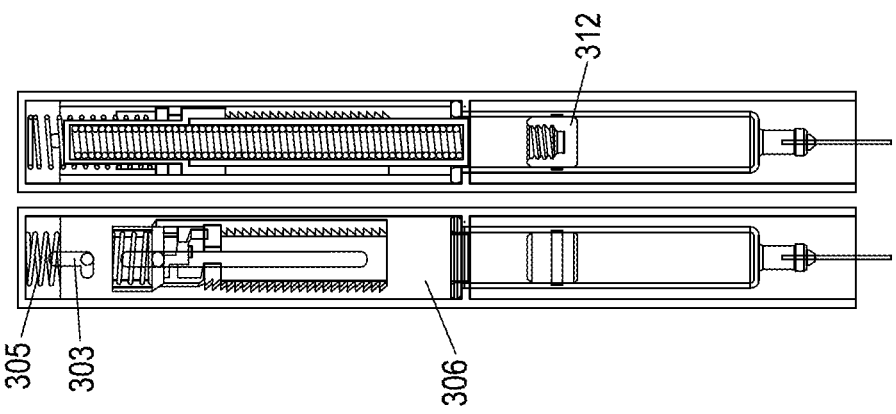
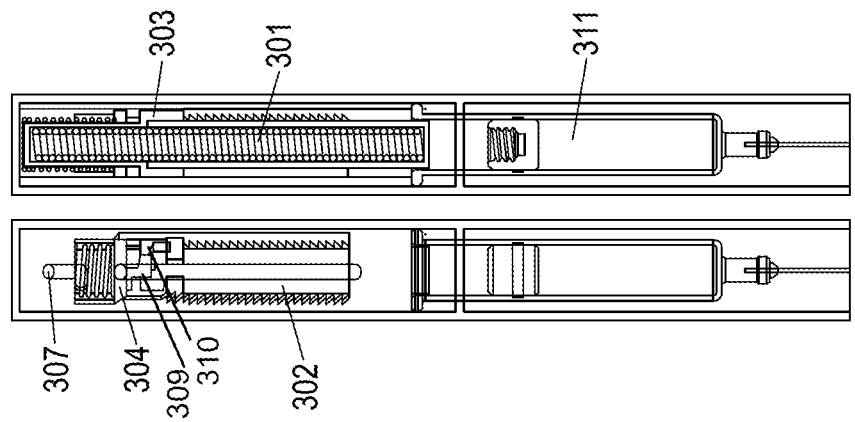

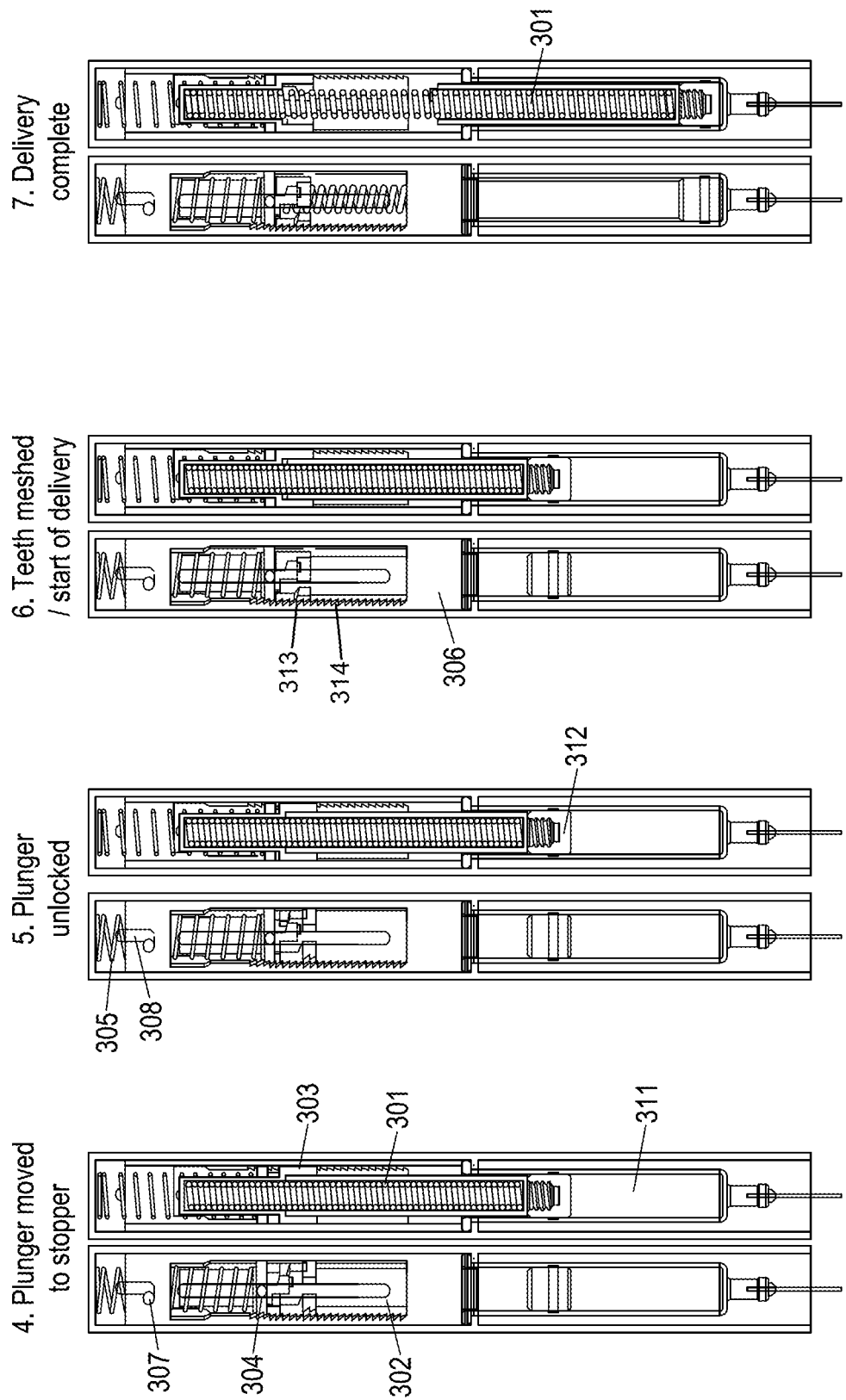

INJECTION DEVICE WITH GAP REDUCTION MECHANISM

CROSS-REFERENCE TO RELATED APPLICATIONS

The present application represents the United States National Stage of International Application No. PCT/GB2018/050663, filed Mar. 15, 2018, which claims priority to British Patent Application Serial No. GB 1704136.9, filed Mar. 15, 2017, and entitled, "INJECTION DEVICE WITH GAP REDUCTION MECHANISM," the contents of which are incorporated herein by reference in their entirety.

TECHNICAL FIELD

This invention relates to injection devices for delivering a dose of medicament from a syringe. In particular, though not necessarily, the invention relates to an autoinjector type device which facilitates powered or power assisted needle insertion and drug delivery.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a drive spring (for example a compression spring) which is held in an energised (or primed position) prior to release by the trigger.

An injection device of the autoinjector type is described in WO2016/189286. The actuation mechanism of this device comprises two springs, a first, relatively weak, insertion spring for moving the syringe through the device housing to insert the needle into the skin and a second, relatively strong, delivery spring for driving the plunger and piston through the syringe body.

WO2016/189286 addresses a known problem with autoinjectors, namely that the force exerted by the insertion spring during the needle insertion phase may be great enough to damage the syringe when it bottoms out against the housing at the end of its travel. The problem is mitigated by incorporating a velocity regulator which limits the velocity of the syringe until it has bottomed out.

SUMMARY

The present invention provides an injection device in accordance with the claims.

Disclosed below there is provided an injection device for delivering a medicament from a syringe contained, in use, within a housing of the device, the device being configured to move the syringe through the housing to cause insertion of a needle of the syringe into a user's skin and to subsequently move a bung of the syringe through a syringe body to deliver medicament through the needle. The device comprises a plunger assembly having a plunger, a delivery spring housing, a first release mechanism that releasably secures the plunger to the delivery spring housing, and a delivery spring located between the plunger and the delivery spring housing and acting between the delivery spring housing and the plunger.

The device may further comprise an insertion spring acting between the housing and the plunger assembly, a syringe driver, a second release mechanism for releasing the plunger assembly from the housing to cause the insertion spring to move the plunger assembly through the housing together with the syringe driver, a stop feature for blocking movement of the syringe driver beyond a certain point in the housing, a third release mechanism for releasing the plunger assembly from the syringe driver upon its engagement with the stop feature to allow the plunger assembly to continue progressing through the housing.

Said first release mechanism may be configured to release the plunger from the delivery spring housing upon contact between the plunger assembly and a bung, to cause the delivery spring to drive separation of the delivery spring housing and the plunger and to thereby apply a delivery force to a bung. The device further comprises a latch mechanism for latching the delivery spring housing at a forward position to substantially prevent rearward movement of the delivery spring housing within the housing following release of the plunger from the delivery spring housing.

BRIEF DESCRIPTION OF THE DRAWINGS

FIGS. 10A to 10G are sequential views of an operating sequence of a further embodiment of an injection device;

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Axial, radial and circumferential are used herein to conveniently refer to the general directions relative to the longitudinal direction of the injection device (or components thereof). The skilled person will, however, appreciated that these terms are not intended to be narrowly interpreted (and for example the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
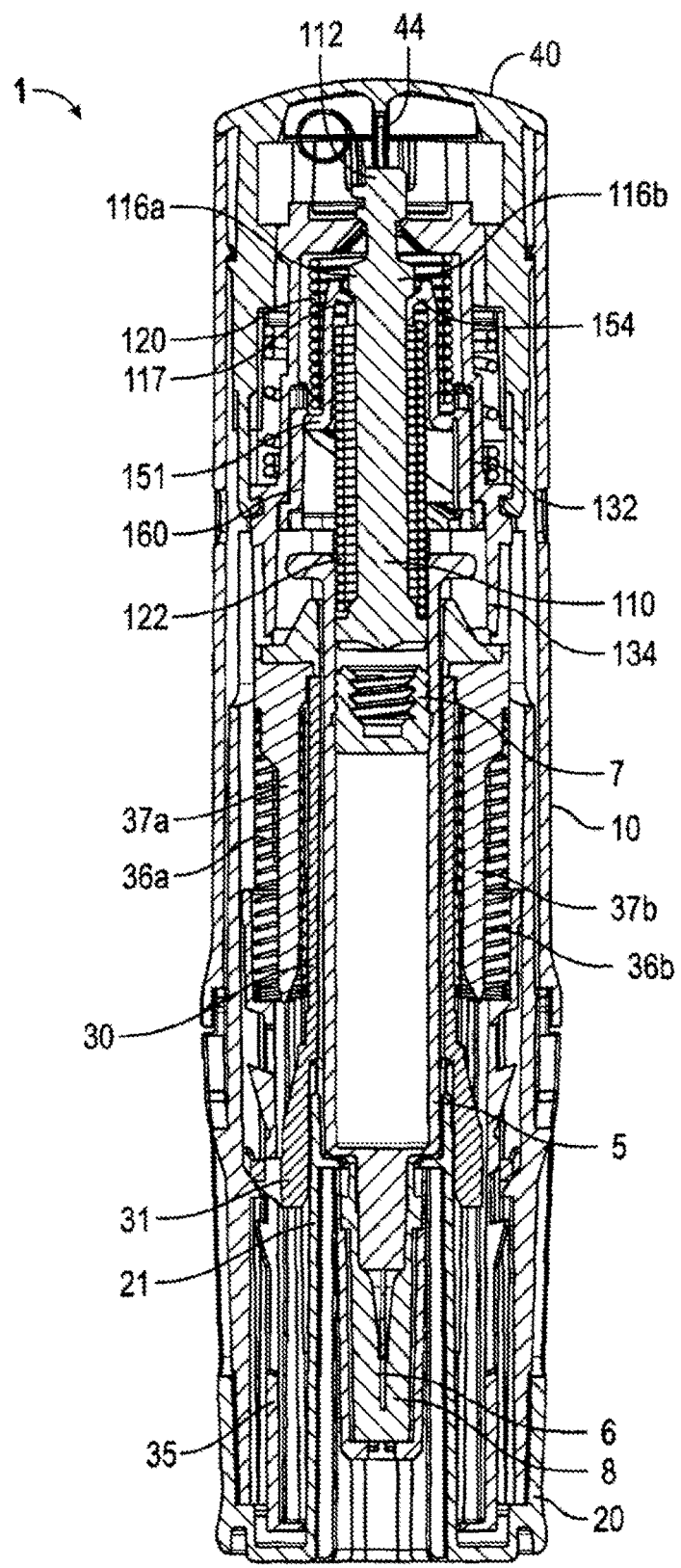
FIG. 1 is a cross-sectional view of a prior art injection device.

FIG. 1 shows a cross-sectional view of a prior art autoinjector 1 as disclosed in WO2016/189286. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may be initially protected (so as to remain sterile) by a removable needle shield or "boot" 8. The illustrated autoinjector 1 is generally intended to be a single use device and, therefore, the view of FIG. 1 may typically represent a fully assembled, ready to use device as provided to an end user. A cap 20 is provided which closes the forward end of the autoinjector 1 prior to use. The cap 20 includes an internal formation, comprising rearwardly extending members 21, arranged to engage the removable needle shield 8 of the syringe 5 such that removal of the cap 20 from the housing 10 during use also removes the removable needle shield 8 from the syringe 5.

The autoinjector 1 comprises a forward subassembly in a forward portion of the housing 10 and a rearward assembly in a rearward portion of the housing 10. The two housing portions may be snap fit together, about the syringe, during assembly. The forward subassembly comprises the components which surround and/or are initially forward of the syringe 5. The rearward subassembly comprises those components which are initially rearward of the syringe 5.

A forward portion of the housing 10 contains a syringe carrier 30 for movably mounting the syringe within the housing 10 to enable automatic needle penetration. It is noted that prior to the removal of the cap 20, the rearwardly extending members 21 of the cap 20 underlie spring fingers 31 of the syringe carrier 30. This arrangement thus prevents inward movement of the spring fingers 31 prior to removal of the cap 20 and, therefore, blocks unlatching of the syringe carrier 30 and prevents movement relative to the housing 20.

A needle shroud 35 is also provided and arranged to shroud the needle after use (when the syringe 5 and syringe carrier 30 are in a forward position) to prevent needle stick injuries. The shroud 35 is be activated by a pair of side-by-side shroud springs 36a, 36b carried on respective spring guides 37a, 37b. Operation of the shroud 30 and carrier 35 is not described here in any detail. However, it is noted that the arrangement substantially corresponds to the arrangement described in WO2012/085580.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

Figure 2:
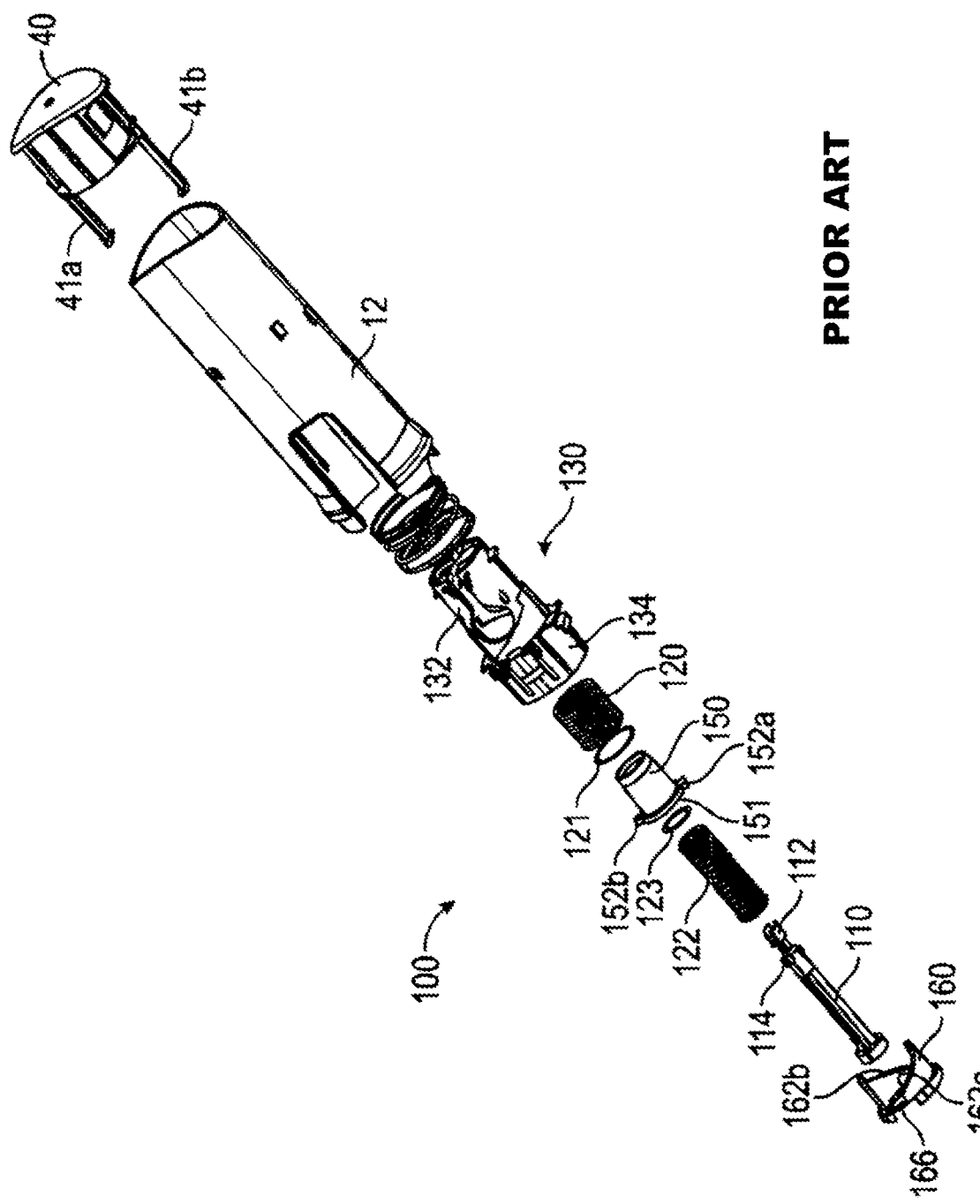
FIG. 2 is an exploded view of a rear section of a prior art injection device.

The rearward portion of the housing 10 also includes a drive mechanism 100, best seen in FIG. 2. The drive mechanism 100 includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 is substantially as described, for example, in WO2012/049484 and WO2015/011488.

The actuation mechanism will now be described in further detail with particular reference to FIGS. 2 and 3 to 6.

FIG. 2 shows an exploded view of a rearward subassembly of the autoinjector device 1 (in which it may be noted that the housing 10 includes a discreet rearward housing component 12). In FIG. 3A the housing is omitted for clarity and in FIGS. 3B and 3C only the components directly associated with the velocity regulator are shown for further clarity. As noted above, the actuation mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which is initially retained in position by the pair of arms 41a, 41b. In a central portion of the inner surface of the rearward face of the button 40, a forwardly extending boss 44 is provided which acts to urge the plunger 110 out of engagement with the latch member 130 during activation (in a manner such as that described in the applicants earlier patent applications referred to above).

The boss 44 comprises an arrangement which is in splined engagement with the rearward head 112 of the plunger 110. It will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The actuation mechanism 100 of the autoinjector device 1 also includes a velocity regulator arranged to control or limit the initial velocity of the plunger 110 upon release of the actuation mechanism. The velocity regulator utilises cam members 152a, 152b which travel along cam surfaces 162a, 162b which provides an inclined plane along which the cam members 152a, 152b will travel during actuation.

The cam surfaces 162a, 162b are conveniently provided on a cam body 160 which is engaged with the forward portion 134 of the latch 130 by a snap-fit arrangement including, for example, at least one latch member 166. To ensure proper alignment between the cam body 160 and the latch member 130, an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearwardly of the cam surfaces 162a, 162b on the interior surface of the latch 130 such that when the cam body is assembled with the latch 130, a slot or track 138 is defined (and configured to receive the cam members 152a, 152b). Each of the cam surfaces 162a, 162b is provided with stop 163 at its rearward end (which acts to separate the separate cam paths defined by the cam body 160) and ends with a cut-out or aperture 164 at the forwardmost end of the cam surfaces 162a, 162b.

Figure 3:
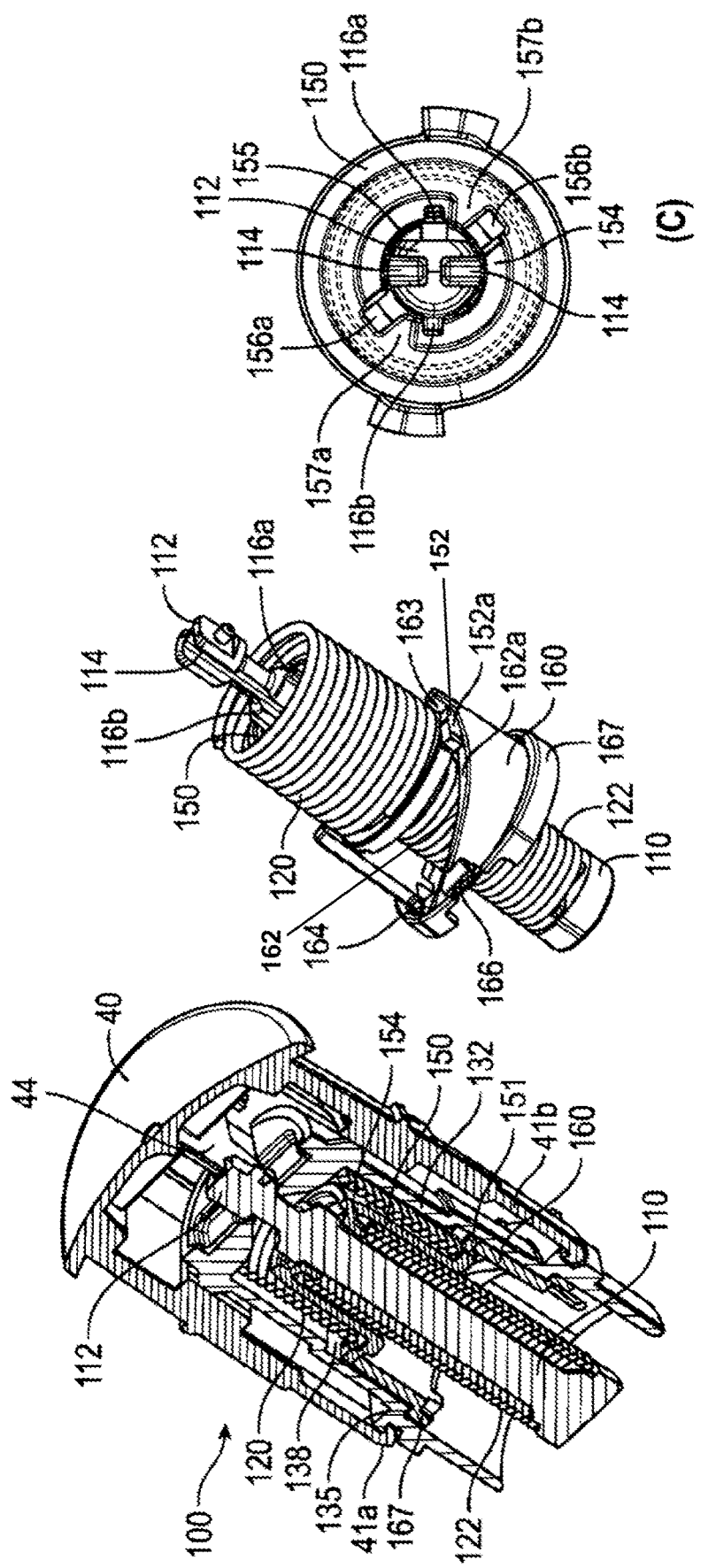
FIG. 3 is a cross-section view and partial end view of an actuation mechanism including a velocity regulator in accordance with an embodiment of the prior art, in a pre-fired state.
Figure 4:
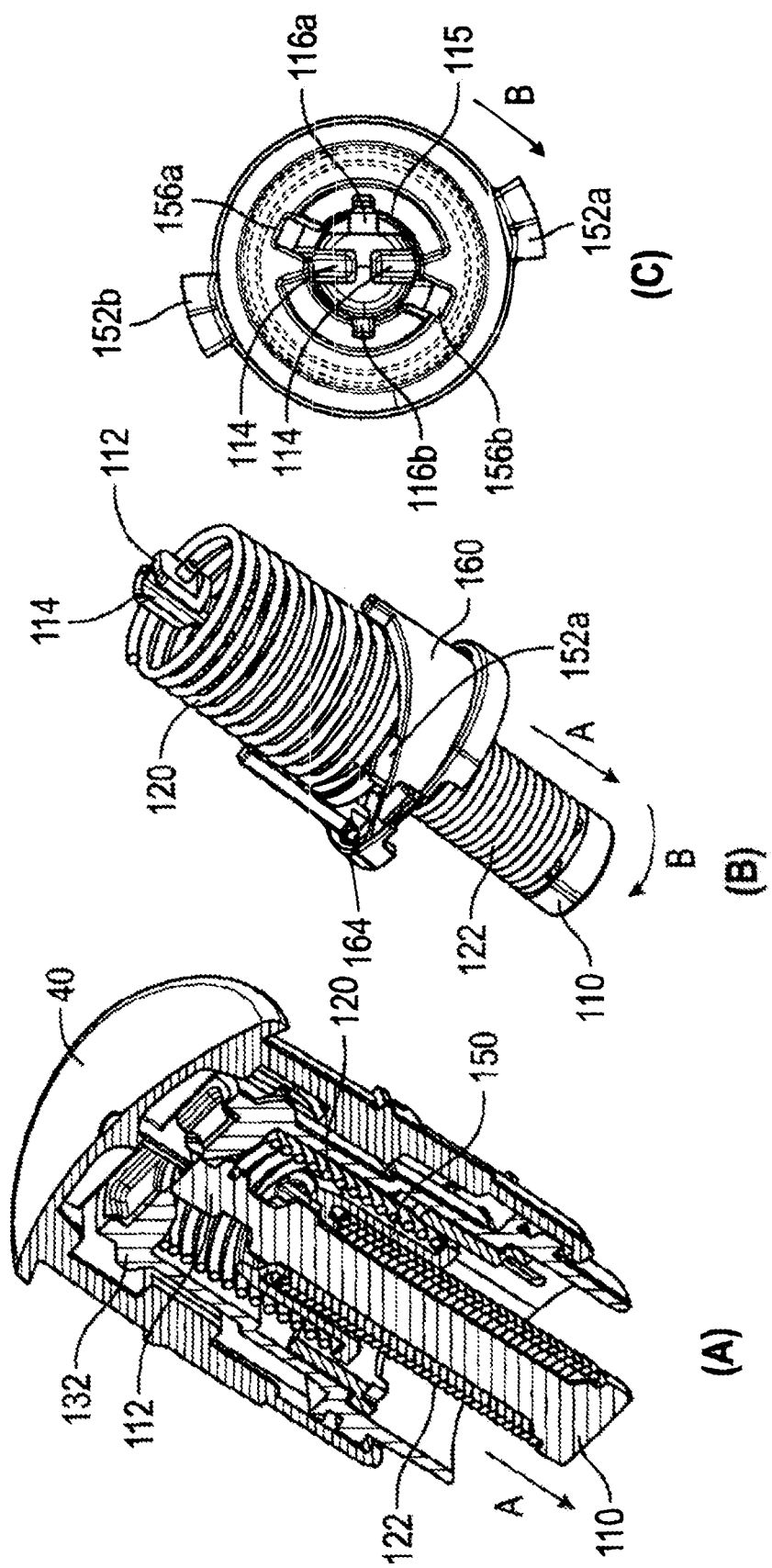
FIGS. 4 to 6 are sequential views corresponding to FIG. 3 during the activation of a prior art autoinjection device.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the actuation mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearwardly, slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly extending projections 116a, 116b which provide a forward facing shoulder 117 is initially engaged with the rearward face of the flange 154. The radial projections 116a, 116b are configured such that they may pass through the radial slots 156a, 156b when the slots 156 and projections 116 are aligned.

The actuation sequence of the mechanism 100 and velocity regulator will now be described with reference to FIGS. 3 to 6. The pre-firing configuration of the actuation mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projection 116 of the plunger 110 is rearwardly positioned relative to the aperture 155 of the collar 150 and the relative rotational position of the plunger 110 and the collar 150 has been set during assembly such that the projections 116 are misaligned with the slots 116 and, in fact, it will be noted that the projections 156 abut against the stop members 157a, 157b of the collar 150. In this initial position the cam members 152a, 152b are positioned at a rearward end of the cam surfaces 162a, 162b and essentially abut against the stops 163 at the rearwardmost end of the cam surfaces 162a, 162b.

In order to activate the device the user urges the trigger button 40 forwardly relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the latch 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152a, 152b to travel along the inclined path of the cam surface 162a, 162b. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152a, 152b travel along the cam surfaces 162a, 162b. The thrust washers 121, 122 prevent or reduce any frictional resistance to the rotation of the collar 150 by the springs 121, 122. As best seen in the end view of FIG. 4C, the resulting relative rotation of the collar 150 causes the aperture 155 to rotate relative to the radial projections 116a, 116b moving the projections off the stop members 157a, 157b and towards the radial slots 156a, 156b.

Figure 5:
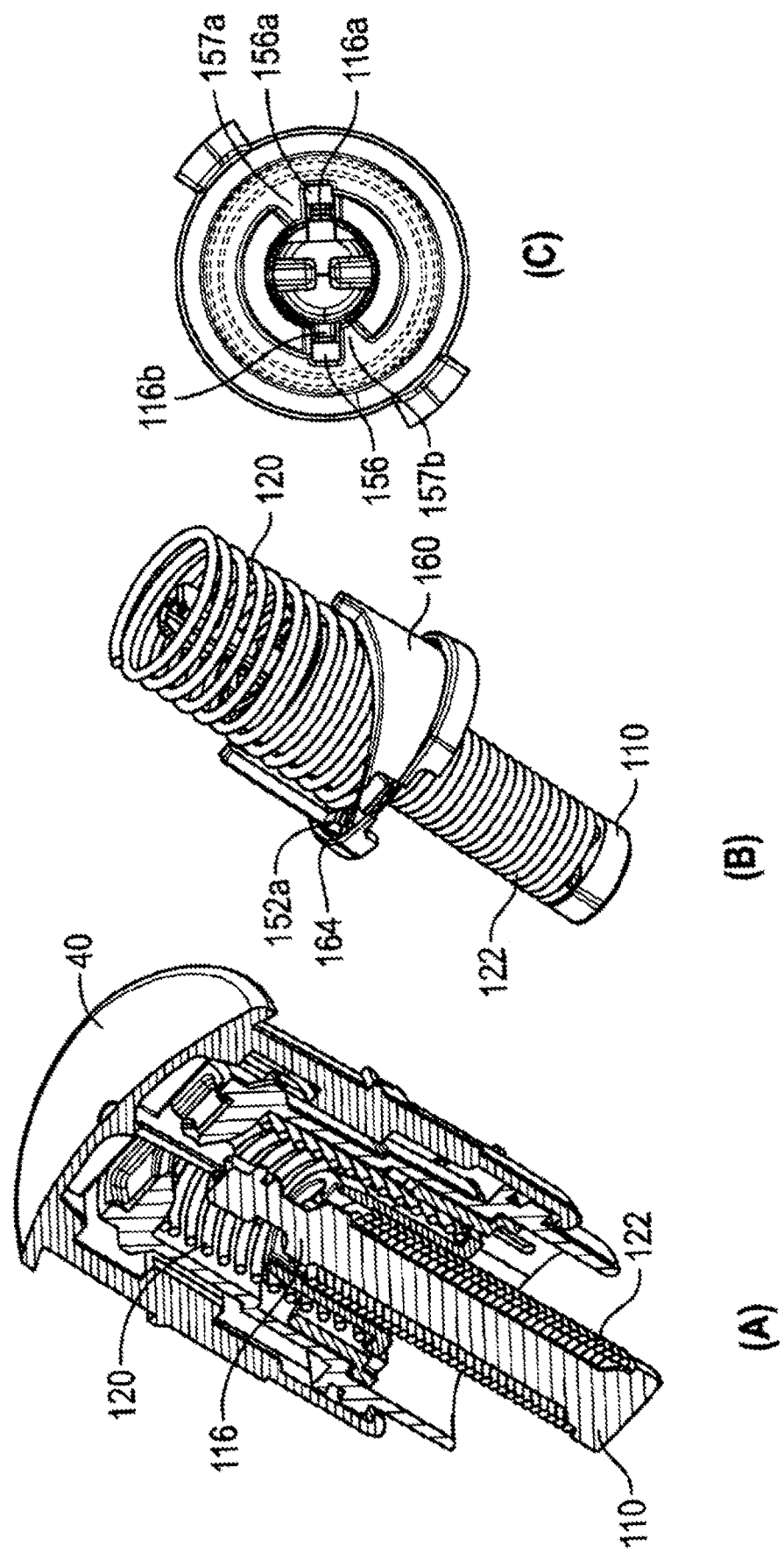

As the plunger 110 and collar 150 continue to move forwardly, the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156a, 156b have rotated into alignment with the radial projections 116a, 116b and the cam members 152a, 152b have also reached the end of the cam surface 162a, 162b and have moved into alignment with the cut-out/aperture 164 at the end of the cam path.

Figure 6:
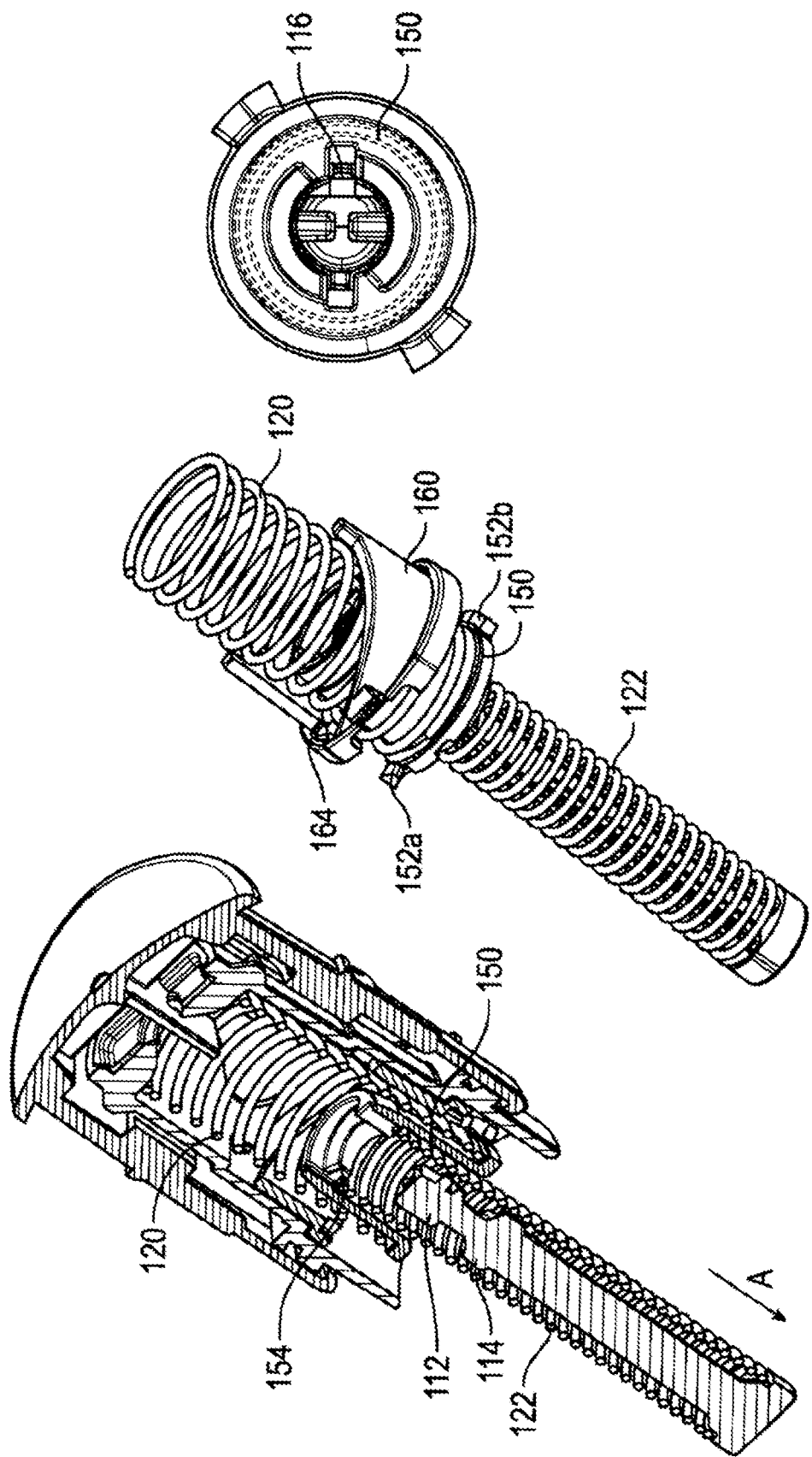

Accordingly, as shown in FIG. 6, the velocity regulator may now disengage so as to allow the plunger to continue freely forward (continuing in the direction of arrow A). In this forward movement the plunger 110 moves forward relative to the collar 150 due to the radial projections 116a, 116b passing through the radial slots 156a, 156b and the collar 150 is also allowed to pass forwardly of the cam body 160 due to the cam members 152a, 152b passing through the cut-outs 164. In other words, both the collar 150 and plunger 110 are disengaged and the collar 150 and cam body 160 are disengaged. In the illustrated embodiment the disengagements both occur substantially simultaneously (although the skilled person will appreciate that this may depend on the particular sequencing required). Once the radial projections 116a, 116b have passed through the radial slots 156a, 156b, the second drive spring 122 is free to expand and push against the collar 150 and plunger 110. The collar 150 is also free from the velocity regulator, and the first drive spring 120 and second drive spring 122 act on the plunger.

Once the velocity regulator is disengaged, the forward motion of the plunger 110 is no longer regulated (but the skilled person will appreciate that the plunger may now be pressing against the medicament within the syringe 5 such that its motion is naturally damped). The forces exerted by the springs 120, 122 on the plunger and the collar are dependent on the relative strengths of the first spring 120 and second spring 122, as well as the damping force provided by the medicament through the plunger 110. The axial motion of the collar 150 once the collar 150 has passed through the velocity regulator is therefore application-dependent.

Although the device has been described above with reference to one embodiment, it will be appreciated that various changes or modifications may be made. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed. Whilst the illustrated example includes two opposing counter-surfaces the skilled person will appreciate that more or less features may be utilised.

In the illustrated device the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

Despite the advances achieved with the prior art autoinjection devices, a problem remains as a result of the variable fill levels of syringe bodies. As a result of this variation it is not possible to precisely define the point at which the delivery spring should be deployed with full force for medicament delivery, relative to the housing.

Some mechanism is therefore required to regulate the velocity of the plunger under the action of the delivery spring until contact has been made with the bung within the syringe body. One way to achieve this is to implement a sensor within the plunger which detects contact with the bung. The velocity regulator is applied up to the point at which contact is sensed and thereafter is removed.

Figure 7:
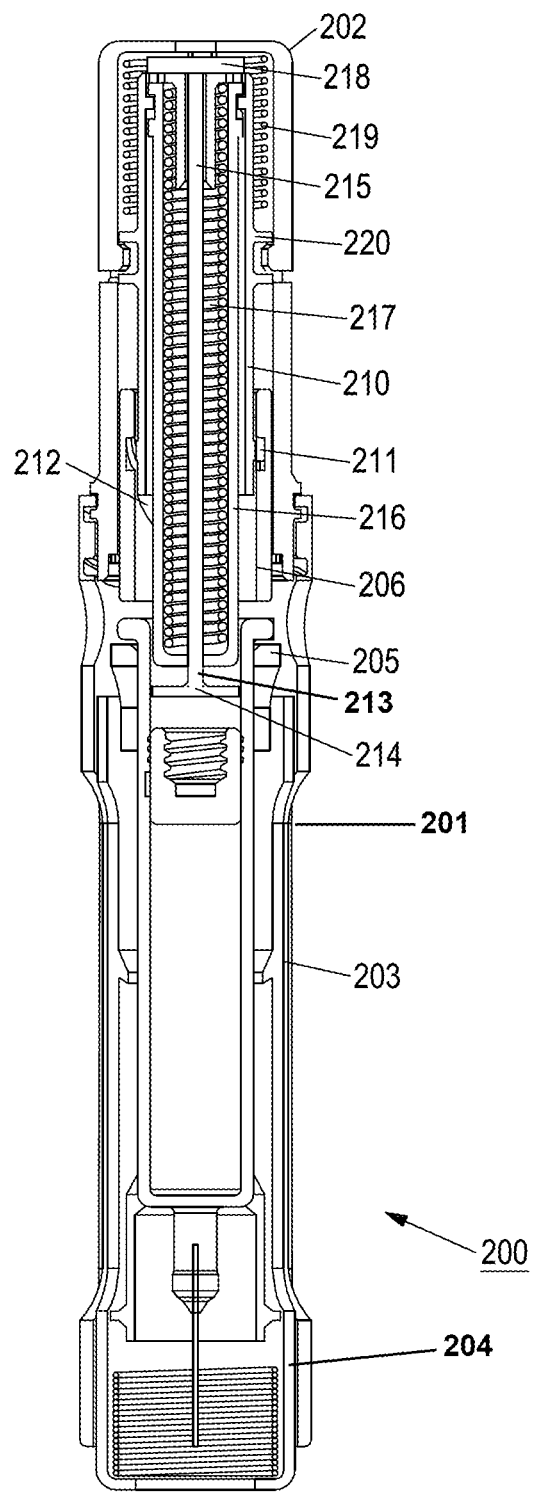
FIG. 7 is a cross-sectional view of an injection device in a pre-fired state.
Figure 8:
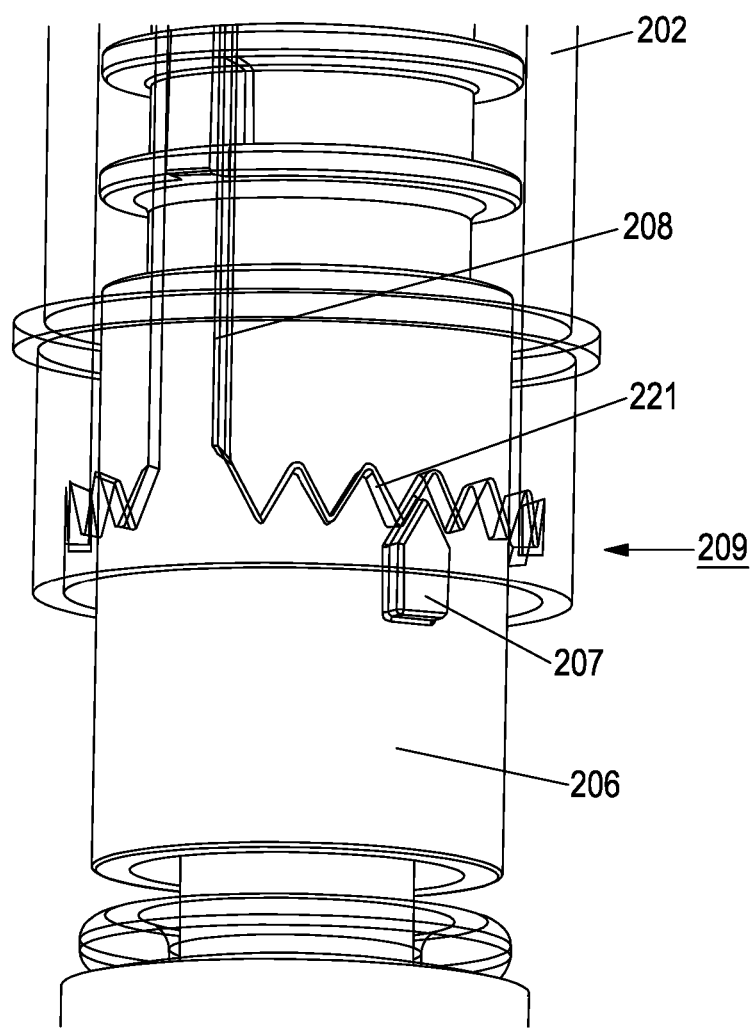
FIG. 8 is a side view of a gap reduction sleeve.

FIG. 7 shows a cross-sectional view of an injection device or autoinjector 200 in accordance with an embodiment of the invention. The autoinjector in FIG. 7 is in a pre-fired state and comprises a housing 201 comprising upper and lower housing parts 202, 203 secured together. A lock-out shroud 204 is slidably mounted within the lower housing part 203. Located within the lower housing part is a syringe carrier 205 which supports the syringe body within the housing. Located principally within the upper housing part is a velocity regulator collar ("syringe driver") 206 having provided on its outer surface a projecting tooth 207. This is best seen in FIG. 8 which also shows in semi-transparent form the upper housing part 202. As can be seen from FIG. 8 the upper housing part 202 has a recessed track 208 formed in its inner surface. This track 208 extends axially along the upper housing part and opens into a circumferentially extending recessed region 209 at the end of the upper housing part. A series of teeth 221 are provided around the upper surface of the region 209.

Referring again to FIG. 7, a delivery spring housing 210 is located within the upper housing part, with its lower region being located within the velocity regulator collar 206. A projection 211 is formed on an outer surface of the delivery spring housing 210 and is engaged with a helical track 212 formed on an inner surface of the collar 206.

The device comprises a plunger assembly 213 having a plunger head 214 and a central shaft 215. The central shaft 215 is located within a cylindrical sleeve 216, and between the central shaft 215 and the sleeve 216 there is provided a delivery spring 217. A cap 218 releasably secures the top of the sleeve 216 to the delivery spring housing 210. In the pre-fired state of FIG. 7 the cap 218 prevents the delivery spring 217 from pushing the sleeve 216 and the delivery spring housing 210 apart.

The injection device also comprises an insertion spring 219 acting between the top of the upper housing part 202 and a shoulder 220 of the delivery spring housing 210. Although not shown in detail in the Figures, the insertion spring 219 is maintained in a compressed state by one or more features of the lock-out shroud 204 which, in the pre-fired state of FIG. 7, block the carrier 205 from moving down through the housing under the force exerted by the insertion spring 219.

Figure 9D:
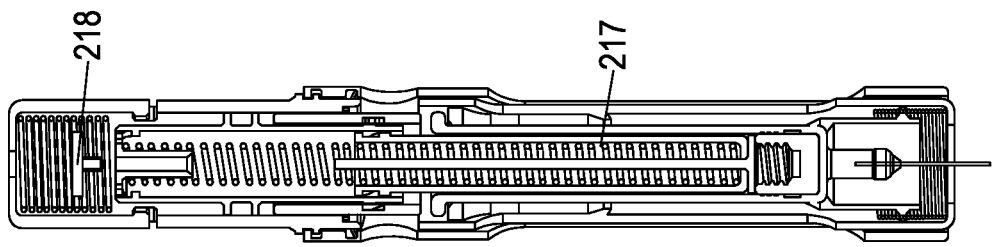
FIGS. 9A to 9D are sequential views corresponding to FIG. 7 during activation of an autoinjection device.
Figure 9C:
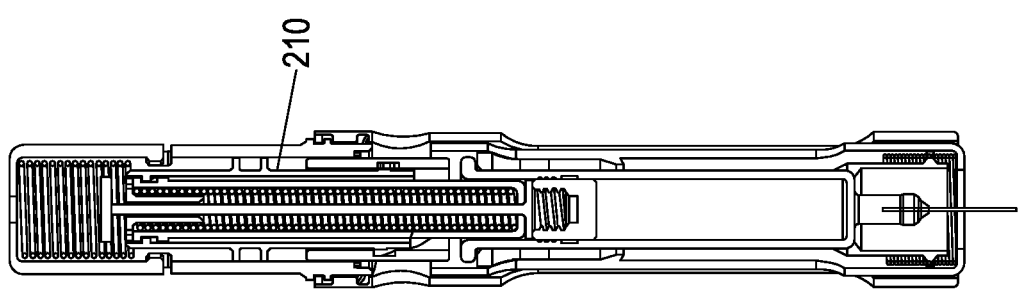

In order to initiate insertion and deliver, the user pushes the end of the lock-out shroud 204 against the skin, pushing the lock-out shroud 204 into the lower housing part 203. The relative movement of the lock-out shroud 204 releases the block on the syringe carrier 205 and therefore the syringe body. The insertion spring 219 is acting on the delivery spring housing 210 which in turn presses down on the velocity regulator collar 206 via the engagement of the projection 211 with the helical track 212. As the velocity regulator collar 206 is at this stage prevented from rotating, both the delivery spring housing 210 and the velocity regulator collar 206 move together through the housing, pushing the sleeve 216, compressed delivery spring 217 and plunger cylinder with them. It will be apparent that the end of the velocity regulator collar 206 is pressing on the top end of the syringe body which is also moved down through the lower housing part 203, causing the needle to be pushed out of the end of the lower housing part 203 into the user's skin. After a certain travel distance, the syringe carrier 205 hits against a stop feature preventing further movement of the carrier 205 and the syringe body. This defines the insertion depth of the needle. This operating state of the device is shown in FIG. 9A.

Engagement of the syringe carrier with the stop feature coincides with the exiting of the tooth 207, formed on the velocity regulator collar 206, from the track 208 and entering the recessed region 209 at the end of the upper housing part. Due to the continuing force downward exerted by the insertion, the tooth 207 is pushed down relative to the series of teeth that are provided around the upper surface of the recessed region 209 and the velocity regulator collar 206 is therefore now free to rotate within the housing. The velocity regulator collar 206 cannot move any further in the axial direction as it is blocked from doing so by its engagement with the syringe body.

As the velocity regulator collar is now free to rotate, the delivery spring housing 210 can begin to move axially down through the velocity regulator collar 206 under the force of the insertion spring acting on it. This causes the sleeve 216 and plunger 213 to continue their downward axial motion until the plunger head 214 meets the bung within the syringe body. However, during this phase the velocity of the plunger is regulated by the relative rotation between the velocity regulator collar 206 and the delivery spring housing 210.

Figure 9B:
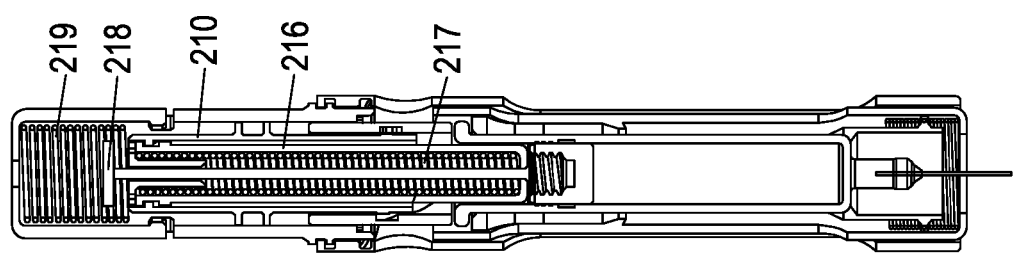
Figure 9A:
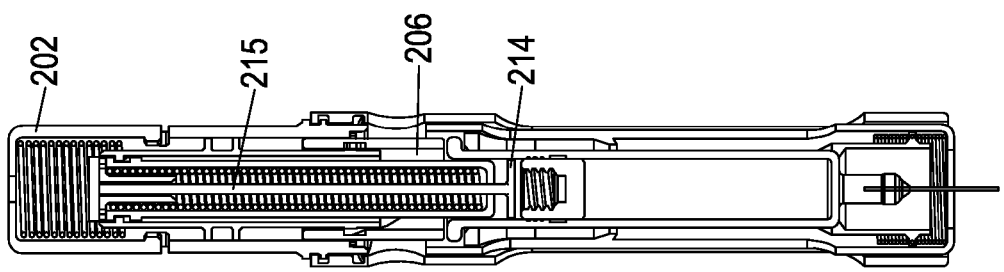

As shown in FIG. 9B, the effect of the plunger head hitting the bung is to exert a force on the cap 218 via the central shaft 215. The upward movement of the cap disengages the cap from the central shaft and also disengages the delivery spring housing 210 from the sleeve 216, freeing the delivery spring to push the delivery spring housing 210 and the sleeve 216 apart. An initial small upward movement of the delivery spring housing 210 brings the projecting tooth 207 of the collar 206 into engagement with the teeth 221 provided around upper housing part 202 (illustrated by the change in configuration from that of FIG. 9B to that of FIG. 9C). This now blocks further upward movement of the delivery spring housing 210 within the housing 201. The force exerted by the delivery spring now urges the cylinder 216 downward together with the plunger 213 which is now pressed against the bung within the syringe body. Medicament is now delivered through the inserted needle until the bung reaches the bottom of the syringe body. This is the operational state shown in FIG. 9D.

Figure 11:
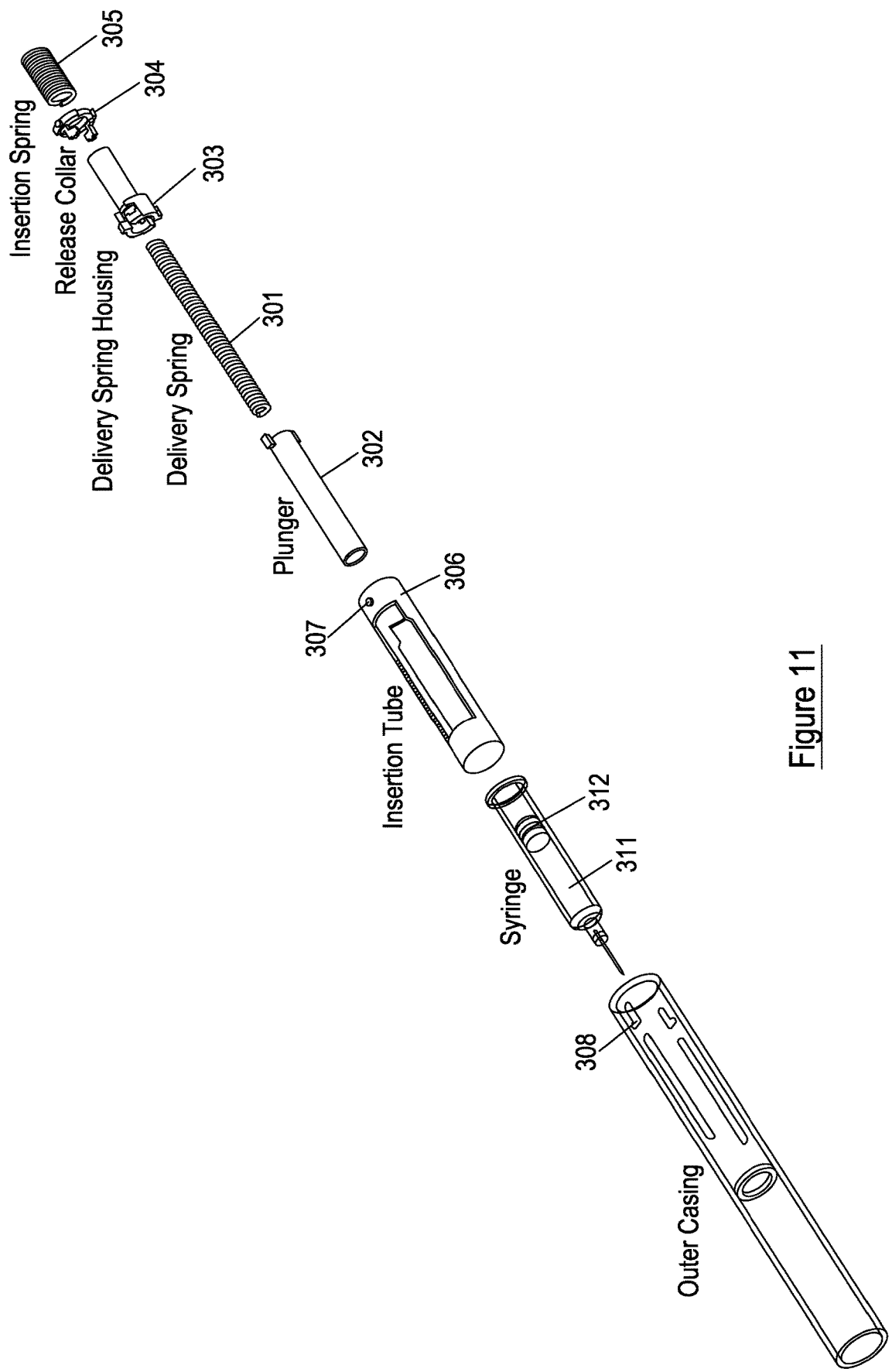
FIG. 11 is an exploded view of the injection device of FIGS. 10A to 10G.
Figure 12:
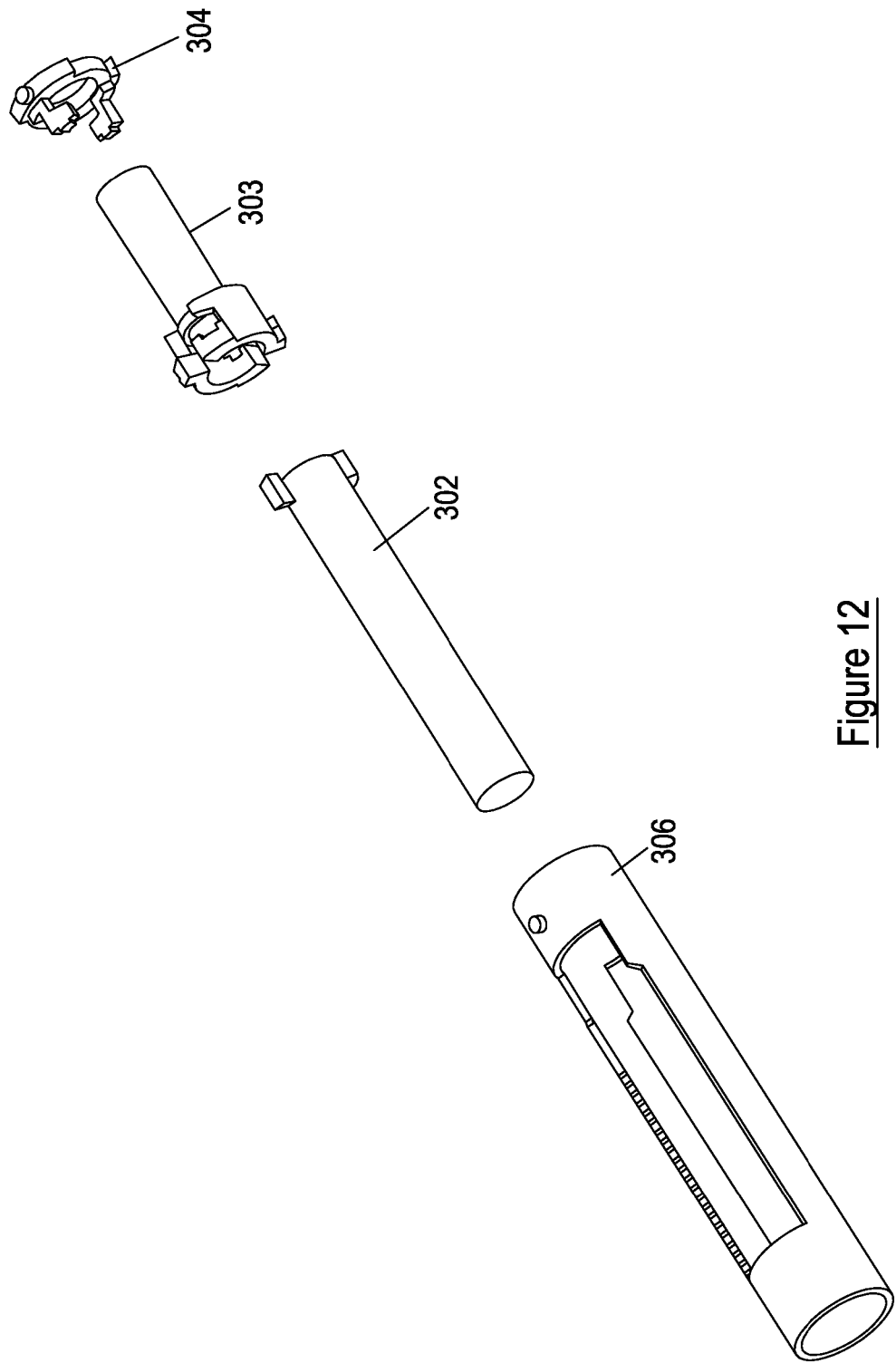
FIG. 12 is an exploded view of the delivery mechanism of the injection device of FIGS. 10A to 10G.

FIGS. 10A to 10G illustrate an operating sequence of a further embodiment of an injection device having a mechanism for closing the gap between the plunger and the bung with a controlled velocity. Certain components of the device are illustrated in an exploded view in FIG. 11 and in more detail in FIG. 12. In this device 300, the delivery spring 301 is initially confined by engagement of the plunger 302 with a delivery spring housing 303 via a release collar 304. During the insertion phase, these components move together, in an axial direction, under the force exerted by the insertion spring 305, together with an insertion tube 306. The insertion tube 306 is confined to move only axially by engagement of a projection 307, formed on an outer surface of the tube, with an axial section of a track 308 provided on an inner surface of the housing. In this state, a tangentially directed shoulder 309 formed on the release collar 304 is engaged with a ledge 310 formed on the insertion tube 306. The shoulder 309 and the ledge 310 are oppositely angled so as to exert a relative rotational force. Of course, both components are prevented from rotating at this stage.

Figure 13:
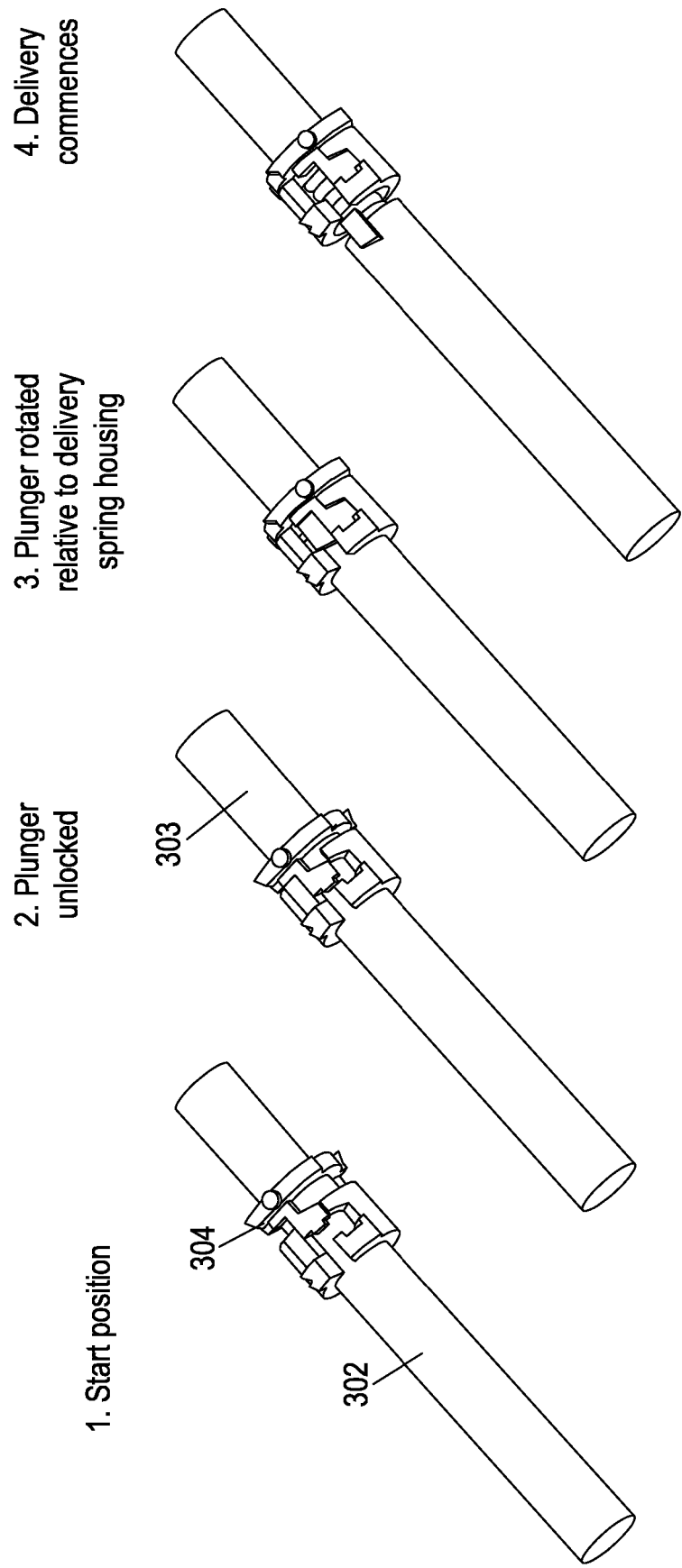
FIGS. 13A to 13D are sequential views of an operating sequence of the delivery mechanism of the injection device of FIGS. 10A to 10G.

When the syringe body 311 bottoms out on certain stop features within the housing, the insertion tube 306 cannot move any further in the axial direction and the insertion phase is completed. At this point, the projection 307 provided on the insertion tube 306 encounters a circumferentially extending section of the track 308, permitting the insertion tube to rotate to a small extent under the force exerted by the release collar 304, disengaging the release collar 304 from the insertion tube 306. The release collar 304 remains pressed down against the delivery spring housing 303 and both components, together with the plunger 302, are pushed down relative to the syringe body 311, under the continued force of the insertion spring 305. This causes the head of the plunger 302 to close the gap with the bung 312 until contact is made. At this point, the plunger is exerting an upward force on the delivery spring housing 303. Via certain cooperating features, this is converted to a rotational force on the delivery spring housing 303. As the plunger 302 cannot rotate it is the delivery spring housing 303 that rotates, causing a number of tangentially directed teeth 313 formed on the delivery spring housing 303 to mesh with a set of teeth 314 extending axially along the insertion tube. This meshing now prevents rearward axial movement of the delivery spring housing 303. Simultaneously, rotation of the delivery spring housing 303 disengages axial blocking features of the delivery spring housing 303 and the plunger 302. The force of the delivery spring now pushes the plunger 302 downward relative to the delivery spring housing 303. FIG. 13 illustrates in more detail the disengagement sequence of the delivery spring housing 303 and the plunger 302.

The full force of the delivery spring 301 is now exerted on the bung 312 within the syringe body 311 via the plunger 302, causing the bung 312 to move through the syringe body 311, delivering medicament through the needle until the bung 312 hits against the bottom of the syringe body 311.

Figure 14:
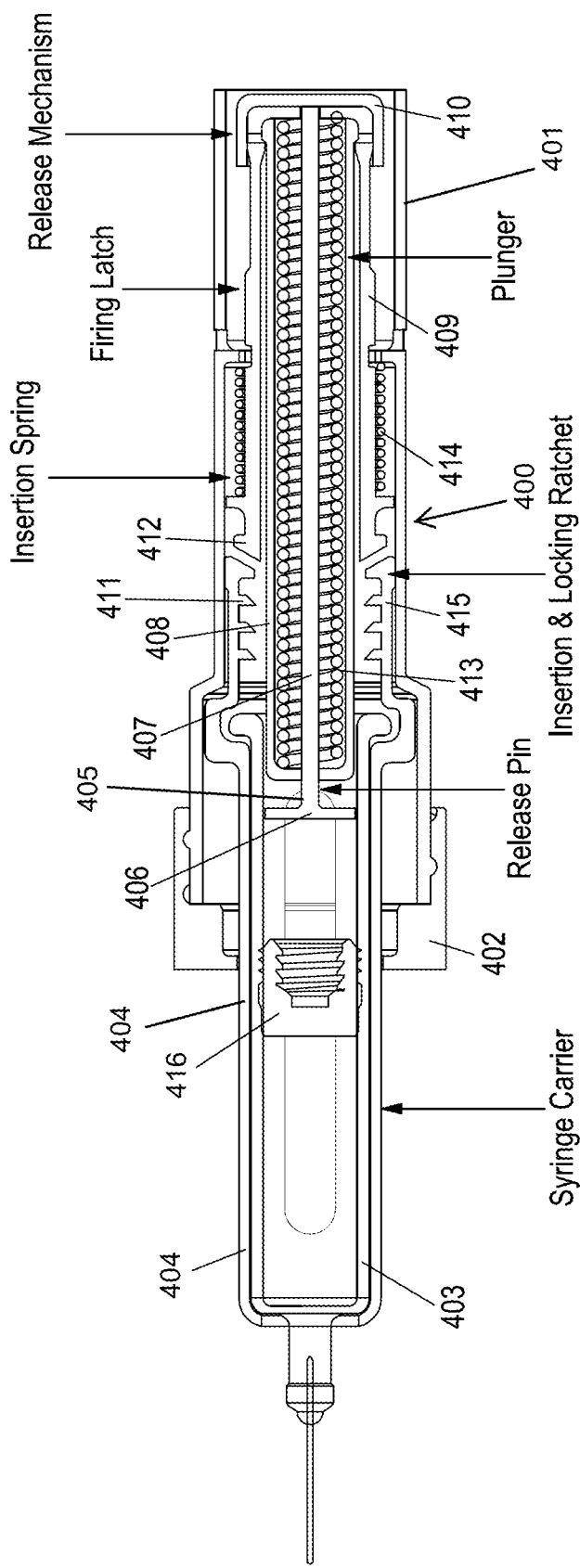
FIG. 14 is a cross-sectional view of an injection device according to a further embodiment.
Figure 15D:
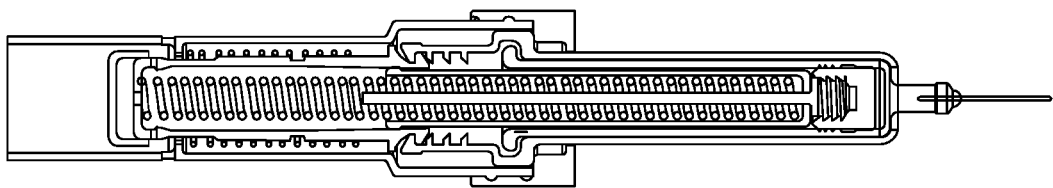
FIGS. 15A to 15D are sequential views of an operating sequence of the device of FIG. 14 with a high syringe fill level.
Figure 15C:
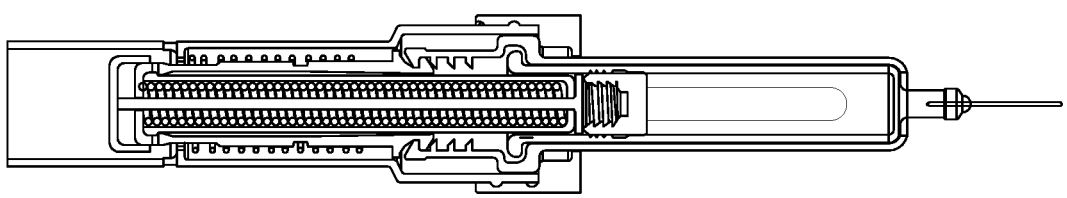
Figure 15B:
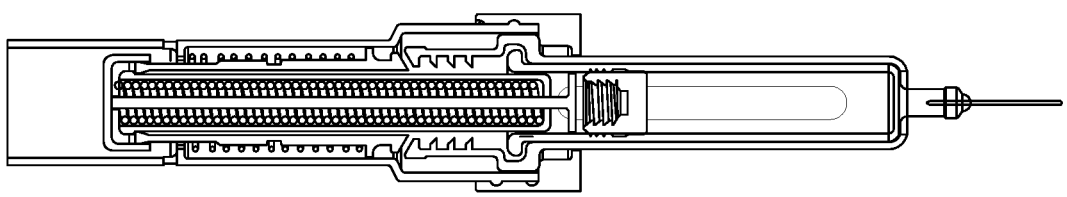
Figure 15A:
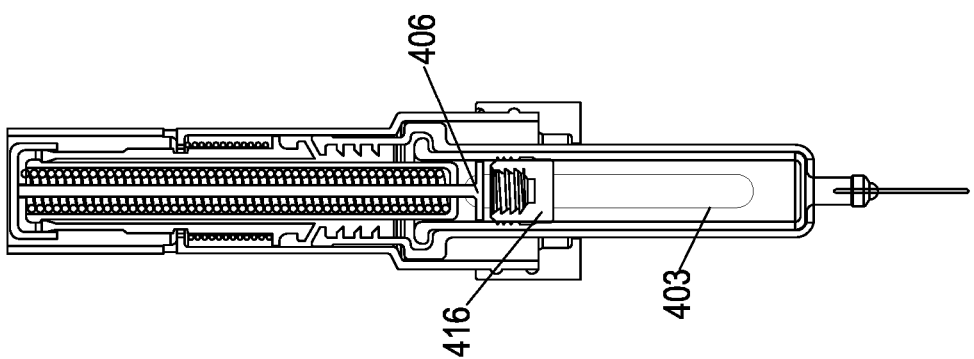
Figure 16D:
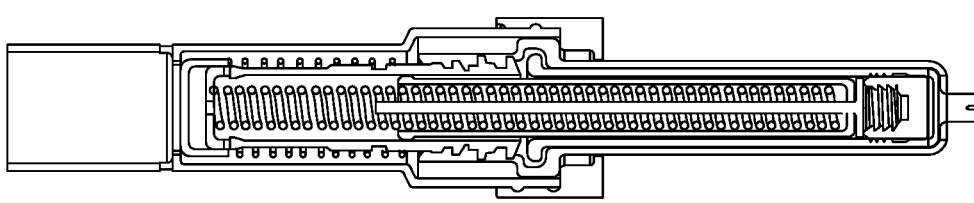
FIGS. 16A to 16D are sequential views of an operating sequence of the device of FIG. 14 with a low syringe fill level.
Figure 16C:
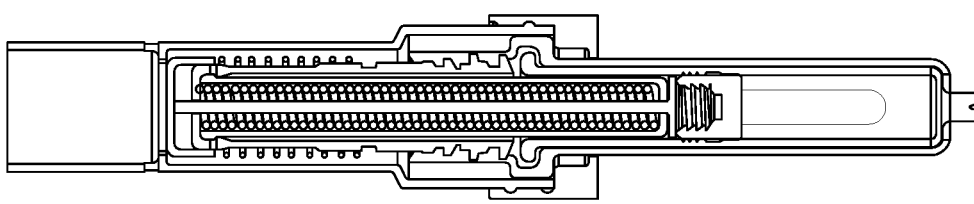
Figure 16B:
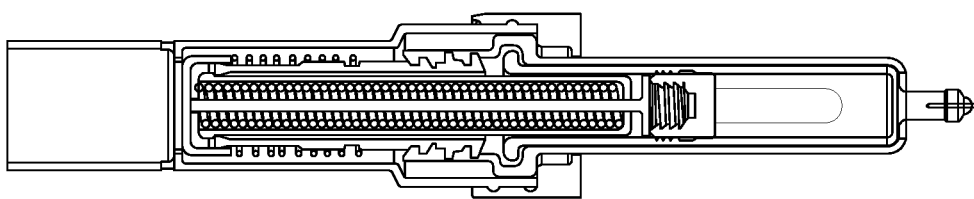
Figure 16A:
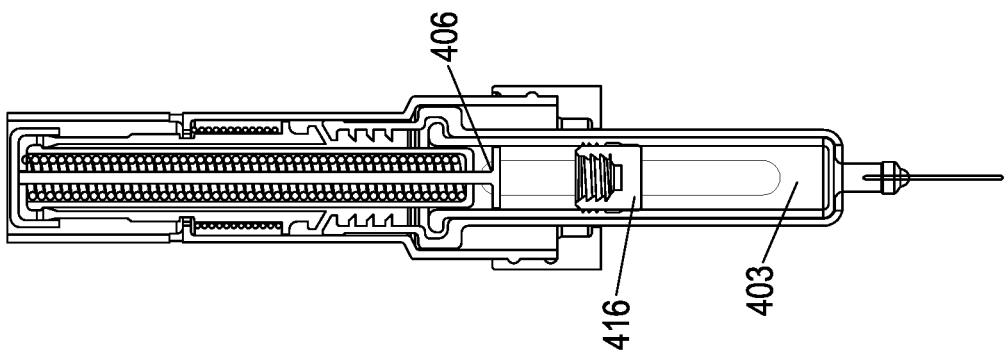

There will now be described a still further embodiment of an injection device having a mechanism for closing the gap between the plunger and the bung with a controlled velocity. This device is illustrated in FIG. 14. Various components are omitted for the sake of clarity including the trigger mechanism. Nonetheless, the skilled person will readily understand what features are required in order to construct a properly functioning device taking into account the devices described above.

The device has a housing 400 comprising an upper housing part 401. The lower housing part is not shown with the exception of a mating and stop part 402. The syringe body 403 is contained within, and moves with, a syringe carrier 404. Similarly to the device described with reference to FIG. 7, a plunger 405 comprises a plunger head 406 and a central shaft 407. The plunger shaft is 407 located within a cylinder 408 with the compressed delivery spring 413 sitting between the shaft 407 and cylinder 408. The cylinder 408 sits within a cylindrical sleeve 409 and is secured to the sleeve 409 by a removable cap 410. The end of the delivery spring 413 abuts at one end the cylinder 408 and at the other end against the cylindrical sleeve 409.

The insertion spring 414 acts between the housing 400 and the sleeve 409. When the device is triggered, the insertion spring 414 pushes the cylindrical sleeve 409 and connected cylinder 408, plunger 405, and compressed delivery spring 413 through the housing 400. The syringe carrier 404 is provided at the end remote from the needle with a pair of flexible legs 415, each leg having on its inner surface a series of ratchet teeth 411. The legs 415 are prevented from flexing outwardly by the upper housing part 401 until the carrier 404 has moved a predefined distance through the housing 400 and further movement of the carrier 404 is blocked, defining the insertion depth. Following this movement, the legs 415 are free to flex outwardly under the force exerted by the front end of the cylindrical sleeve 409. This front end comprises outwardly facing teeth 412 which slide under the flexed legs 415, latching in place with the ratchet teeth 411 as they travel. As the sleeve 409 travels, with the syringe body 403 stopped, the sleeve 409 pushes the plunger 405 through the syringe body 403 until the plunger head 406 contacts the bung 416 in the syringe. As described above, this causes the central shaft 407 of the plunger to push off the cap 410, disengaging the cylinder 408 from the cylindrical sleeve 409. The engagement of the teeth 412 and the ratchet teeth 411 prevents the cylindrical sleeve 409 from being pushed back into the upper housing part 401 by the expansion of the delivery spring 413. Rather, the cylinder 408 and the plunger 405 are pushed forward with the full force of the delivery spring 413, pushing the plunger head 406 and bung 416 through the syringe body 403 to deliver medicament through the needle.

FIG. 15 illustrates various stages of operation of the device. In this example the syringe body 403 has a relatively high fill level resulting in a small initial gap between the plunger head 406 and the bung 416 (in the pre-fired state). FIG. 16 illustrates the same stages of operation but with the syringe body 403 having a relatively low fill level. In the case of the high fill level the teeth 412 engage with the ratchet teeth 411 close to the top of the syringe carrier 404. In contrast, in the case of the relatively low fill level, the teeth 412 engage with the ratchet teeth 411 close to the bottom of the syringe carrier 404.

It will be appreciated by the person of skill in the art that various modifications may be made to the above described embodiments without departing from the scope of the present invention.

The invention claimed is:

1. An injection device for delivering a medicament from a syringe contained, in use, within a housing of the device, the device being configured to move the syringe through the housing of the device to cause insertion of a needle of the syringe into a user's skin and to subsequently move a bung of the syringe through a syringe body to deliver medicament through the needle, the device comprising:
   a plunger assembly having:
      a plunger;
      a delivery spring housing;
      a release mechanism comprising a cap that releasably secures the plunger to the delivery spring housing;
      a delivery spring located between the plunger and the delivery spring housing and acting between the delivery spring housing and the plunger;
      an insertion spring acting between the device housing and the plunger assembly,
         said insertion spring being configured to move the plunger assembly through the device housing upon release of the plunger assembly from the device housing,
         said release mechanism being configured to release the plunger from the delivery spring housing upon contact between the plunger assembly and the bung, to cause the delivery spring to drive separation of the delivery spring housing and the plunger and to thereby apply a delivery force to the bung, and
         the delivery spring housing being latched at a forward position to substantially prevent rearward movement of the delivery spring housing within the device housing following release of the plunger from the delivery spring housing.

2. The injection device according to claim 1, further comprising:
   a syringe driver;
   wherein the syringe driver, upon engagement with the syringe body, is blocked from movement beyond a certain point in the device housing;
   wherein the plunger assembly is released from the syringe driver upon engagement of the syringe driver with the syringe body to allow the plunger assembly to continue progressing through the device housing; and
   wherein the insertion spring moves the plunger assembly through the device housing further together with a syringe carrier.

3. The injection device according to claim 2, wherein said syringe driver is confined to move axially but not rotationally within the device housing substantially up to a point where further axial movement of the syringe driver is blocked, whereupon the syringe driver is able to move rotationally, and said delivery spring housing is confined to move axially with the syringe driver until rotation of the syringe driver is permitted.

4. The injection device according to claim 3, wherein the delivery spring housing is latched by a latch mechanism, and wherein said latch mechanism comprises interengaging teeth of the syringe driver and the device housing.

5. The injection device according to claim 4 and comprising a velocity regulator comprising the syringe driver and the delivery spring housing for regulating a velocity of the plunger assembly following release of the plunger assembly from the syringe driver.

6. The injection device according to claim 3 and comprising a velocity regulator comprising the syringe driver and the delivery spring housing for regulating a velocity of the plunger assembly following release of the plunger assembly from the syringe driver.

7. The injection device according to claim 2, wherein the delivery spring housing is latched by a latch mechanism, and wherein said latch mechanism comprises one or more teeth on the delivery spring housing and a set of axially spaced teeth on the syringe driver or vice versa.

8. The injection device according to claim 7 and comprising a velocity regulator comprising the syringe driver and the delivery spring housing for regulating a velocity of the plunger assembly following release of the plunger assembly from the syringe driver.

9. The injection device according to claim 2, further comprising a velocity regulator comprising the syringe driver and the delivery spring housing for regulating a velocity of the plunger assembly following release of the plunger assembly from the syringe driver.

10. The injection device according to claim 2, wherein said plunger comprises a plunger shaft extending axially through a substantially cylindrical sleeve, the delivery spring being located between the plunger shaft and the sleeve.

11. The injection device according to claim 1, wherein said plunger comprises a plunger shaft extending axially through a substantially cylindrical sleeve, the delivery spring being located between the plunger shaft and the sleeve.

12. The injection device according to claim 11, wherein the sleeve is located within the delivery spring housing and wherein said plunger shaft is releasably secured to the delivery spring housing via said sleeve.

13. The injection device according to claim 11, wherein the cap is connected to the plunger shaft, the cap releasably securing a top of the sleeve to the delivery spring housing.

14. The injection device according to claim 13, wherein a plunger head is pushed through the syringe body until the plunger head hits the bung to exert a force on the cap via a central shaft, wherein an upward movement of the cap disengages the delivery spring housing from the sleeve freeing the delivery spring to push the delivery spring housing and the sleeve apart.

15. The injection device according to claim 13, wherein the cap additionally disengages from a central shaft.

16. The injection device according to claim 1, wherein the delivery spring housing and plunger rotate relative to one another so as to disengage axial blocking features of the delivery spring housing and the plunger.

17. The injection device according to claim 1, wherein the delivery spring housing includes a plurality of teeth.

18. The injection device according to claim 17, wherein the delivery spring housing is latched by a latch mechanism, and
wherein the latch mechanism comprises an insertion tube and a set of teeth extending axially along the insertion tube, wherein the plurality of teeth of the delivery spring housing mesh with the set of teeth of the insertion tube to prevent rearward axial movement of the delivery spring housing.

19. The injection device according to claim 1, wherein the delivery spring is initially confined by engagement of the plunger with the delivery spring housing via a release collar.

* * * * *